United States Patent [19]

Corcoran et al.

[11] Patent Number: 4,986,963
[45] Date of Patent: Jan. 22, 1991

[54] METHOD OF DISINFECTING CONTACT LENSES WITH PERACETIC ACID

[76] Inventors: Richard A. Corcoran, 2801 Casa de Vida Dr., Aptos, Calif. 95003; James P. Whinston, 760 SW. Vista Ave., Apt. 33, Portland, Oreg. 97205

[21] Appl. No.: 301,810

[22] Filed: Jan. 24, 1989

[51] Int. Cl.$^5$ .................. A61K 31/185; A61L 2/18
[52] U.S. Cl. ................... 422/30; 252/106; 422/28; 424/613; 514/839; 514/840
[58] Field of Search .............. 422/28, 30; 252/106; 424/613; 514/839, 840

[56] References Cited

U.S. PATENT DOCUMENTS

| | | |
|---|---|---|
| 3,681,492 | 8/1972 | Kotzbauer . |
| 3,684,477 | 8/1972 | Blumbergs et al. . |
| 3,873,696 | 3/1975 | Randeri et al. . |
| 3,908,680 | 9/1975 | Krezanoski . |
| 3,912,451 | 10/1975 | Gaglia, Jr. . |
| 3,935,342 | 1/1976 | Lim . |
| 3,989,656 | 11/1976 | Kamiya et al. . |
| 4,046,706 | 9/1977 | Krezanoski ............... 252/542 X |
| 4,051,058 | 9/1977 | Bowing et al. . |
| 4,095,877 | 6/1978 | Stoy et al. . |
| 4,153,349 | 5/1979 | Wichterle . |
| 4,356,100 | 10/1982 | Sherman .................. 252/106 |
| 4,401,582 | 8/1983 | Sherman ................ 252/106 X |
| 4,414,127 | 11/1983 | Fu . |
| 4,450,264 | 5/1984 | Cho . |
| 4,451,624 | 5/1984 | Howes . |
| 4,473,550 | 9/1984 | Rosenbaum et al. . |
| 4,490,389 | 12/1984 | Nelson et al. .......... 252/106 X |
| 4,510,065 | 4/1985 | Sherman ................... 252/106 |
| 4,521,375 | 6/1985 | Houlsby ..................... 422/29 |
| 4,568,517 | 2/1986 | Kaspar et al. ............... 422/30 |
| 4,581,374 | 4/1986 | Nelson et al. .......... 252/106 X |
| 4,581,379 | 4/1986 | Nelson et al. .......... 252/106 X |
| 4,585,488 | 4/1986 | Giefer ......................... 422/30 X |
| 4,588,586 | 5/1986 | Kessler et al. . |
| 4,670,178 | 6/1987 | Huth et al. .............. 252/106 X |
| 4,743,447 | 5/1988 | Le Rouzic et al. . |
| 4,748,992 | 6/1988 | Giefer ....................... 252/106 X |
| 4,767,559 | 8/1988 | Kruse et al. ................ 252/106 |

FOREIGN PATENT DOCUMENTS 2584503 1/1987 France .

OTHER PUBLICATIONS

"The Changing Face of Disinfection and Care," *Contact Lens Spectrum*, Apr. 1990: 51–64 at 62, 64.
Solomons, *Organic Chemistry*, 2nd Ed., John Wiley & Sons, N.Y., N.Y. (1980), pp. 70–71.
Turner, *Disinfection, Sterilization and Preservation*, 3rd Ed, Lea & Febiger, Philadelphia, Pa. (1983), pp. 245–246.
Laroche, Derwent Publication #87-044862/07 (Abstract of FR 2584503, published 01/09/87).

*Primary Examiner*—Robert J. Warden
*Assistant Examiner*—Jill Johnston
*Attorney, Agent, or Firm*—Klarquist, Sparkman, Campbell, Leigh & Whinston

[57] ABSTRACT

A method for disinfecting a contact lens contacts the lens with a sterilizing composition comprising about 0.0001% to 10.0% by weight peracetic acid for a time period sufficient to disinfect the lens, and then antiseptically removes the peracetic acid using a peracetic acid removing agent to leave the lens and the remaining composition sterile, biocompatible to the human eye, and isotonic to human tears. The peracetic acid removing agent can be a peracetic acid decomposition catalyst or a peracetic acid neutralizing compound.

5 Claims, No Drawings

METHOD OF DISINFECTING CONTACT LENSES WITH PERACETIC ACID

FIELD OF THE INVENTION

The present invention relates to a method of disinfecting contact lenses with peracetic acid. Following disinfection, the contact lenses and the surrounding solution are treated to decompose, neutralize and remove the peracetic acid, in order to reduce irritation to the eye. In addition, the lenses and surrounding solution are pH neutralized and are made isotonic with human tears. This insure that the lenses will not be irritating upon reinsertion onto the eye, and that no damage to the eye will occur.

BACKGROUND OF THE INVENTION

The present state-of-the-art in contact lenses involves two broad categories of materials: hard or rigid lenses, and soft lenses. Hard lenses were originally made of PMMA(polymethyl metacrylate), but those in widest use now are silicon/acrylates. Silicone/acrylates contain different component ratios (silicone: acrylate) or other additives such as fluorine to make them unique among a large group of related compounds. Soft lenses are generally made of polyhydroxymethylmethacrylate, crosslinked with a variety of compounds to create a lens with distinctive properties. There are other materials and configurations available (and many unique materials not presently available for clinical use), but the foregoing compositions are in widest use.

Although the present invention will primarily be discussed with reference to soft contact lenses, it is equally applicable to hard or other contact lenses.

Soft lenses are extremely hydrophilic by nature, absorbing about 25%–80% of their composition as water. Accordingly, they provide an excellent medium for microbial growth and concentration of contaminants both inside the lens, and on the surface, these microbes and contaminants typically come from the eye, the patient's hands or the solution in which the lenses are stored. As a result, the lenses must be regularly cleaned and disinfected upon removal, but not usually more than once a day.

Cleaning is generally accomplished using a surfactant which is rubbed on the lens using the fingers. This is rinsed off using saline (isotonic NaCl solution) solution. The lenses are then ready to be disinfected.

There are presently three broad categories of disinfection methods. All leave the lenses nearly isotonic to human tears, and at a substantially neutral pH (in order to decrease the potential for irritation upon reinsertion of the lenses on the eye).

The first method uses heat. The lenses are placed in a container with saline, followed by insertion of the container into a heating unit. The temperature in the heating unit is the raised to 80 to 100 degrees centrigrade for 30 minutes to one hour. Thereafter the unit automatically shuts off, and is allowed to cool for an equal length of time before the lenses can be placed on the eyes. One drawback of heat disinfection is that it cannot be used on lenses which are greater than 50% water, or damage to the lens will result. There is also evidence that lenses which are less than 50% water are prematurely aged by the heating process. Furthermore, small amounts of debris and organic material remain on the lenses even after cleaning. These literally become baked on the lenses by the sterilizing heat.

The second disinfection method uses a microbicidal chemical in saline solution. Lenses are placed in the solution for about four hours, rinsed with saline, and reinserted on the eyes. Exemplary microbicides include chlorhexidine, benzalkonium chloride, and polyaminopropyl biguanide. Although this method is a simple and generally effective way to disinfect lenses, many patients are sensitive to the microbicides used above, and cannot use them. Generally recognized sensitivity rates are between 10 to 40% of the general population. "New" Chemical sterilants simply cause the same allergy and sensitivity problems shortly after appearing on the market.

The third and most popular disinfection method uses 3% hydrogen peroxide ($H_2O_2$) to sterilize the lenses, followed by neutralization of the hydrogen peroxide to simple biocompatible products. Neutralization must occur since the eyes can be damaged by hydrogen peroxide, and even 50 ppm $H_2O_2$ may cause mild irritation. A one-step $H_2O_2$ disinfection process involves placing the lenses in a container of hydrogen peroxide and saline which has a platinum catalyst at the bottom to neutralize the $H_2O_2$ while disinfecting the lenses (U.S. Pat. No. 3,912,451). Six hours are required for this process. However, a major disadvantage of this process is that the $H_2O_2$ is neutralized logarithmically (i.e. the concentration of $H_2O_2$ is reduced quite rapidly in the beginning). As a result, effective microbicidal concentrations may not be present long enough to do a good job of disinfection. Even under optimum conditions, $H_2O_2$ is only a fair bactericide, and is not a good sporicide or fungicide.

Several other systems using $H_2O_2$ and a variety of neutralizers (or dilution with saline) involve two or more steps. For example, the lenses are placed in 3% $H_2O_2$ for 5–20 minutes, followed with one or more rinses, and placement in a neutralizer and isotonic saline for 10 minutes to one hour. Drawbacks of this process typically involve a lack of patient compliance or inadequate removal of $H_2O_2$. Some patients forget to complete the second neutralizing step described above, with resultant eye damage, or don't leave the lenses in the $H_2O_2$ long enough for effective disinfection to occur. An additional problem is that many patients do not disinfect their lenses because of the perceived inconvenience of having to complete two steps. Single step systems have a substantially greater compliance rate.

A further problem has recently developed involving the appearance of new microbes and their effect on contact lens users. Two of these microbes includes the AIDS virus and Acanthamoeba. The AIDS virus is a well known, potentially lethal virus which has been isolated in tears. The importance of killing this virus is more pronounced in the doctor's office, where the same lens can be used on many different patients. Present studies indicate that the AIDS virus can be killed by either heat or $H_2O_2$. However, Acanthamoeba is capable of spore formation, and is resistant to $H_2O_2$. However, heat is fairly effective against Acanthamoeba. Acanthamoeba, although rare, causes a particularly painful eye infection, with no acceptable cure at present. It usually results in permanent blindness to that eye. Accordingly, many eye doctors are turning back to heat disinfection, although this method cannot be used with contact lenses having a 50% or greater water content. Furthermore, heat does not kill Bacillus organisms, as discussed in Shovlin J. "Contact Lens Q and A." *Review of Optometry* 1988 (March 15); 125(3): 95.

Thus the three major problems (as seen by today's contact lens practitioner) with existing state-of-the-art contact lens disinfection systems are:

1. PATIENT COMPLIANCE

The regimen should be as simple as possible, with very little time consumption. This tends to rule out any timed or multiple step systems, requiring the long term attention of the patient. However, some patients eye's are quite sensitive, and may require a two-step system or a second rinse in non-preserved saline.

2. SOLUTION TOXICITY OR SENSITIVITY

Toxicity rates are cited in the current literature for various disinfectants and preservations as between 10 to 40%. This is why $H_2O_2$ is so popular since it can be neutralized quite effectively to water and oxygen gas ($H_2O$ and $O_2$). Therefore, a neutralized disinfectant would be the most hypoallergenic, if the decomposed products were biocompatible.

3. EFFECTIVE AGAINST A WIDE VARIETY OF MICROBES AND USEFUL WITH ANY CONTACT LENS.

As shown above, present systems cannot be used with all types of contact lenses, and no one system is effective against all pertinent microbes.

Presently the best systems available are the $H_2O_2$ systems, since they can be used with all contact lenses and can be neutralized to safe decomposition products. The present invention, however, improves considerably on these $H_2O_2$ systems, which have a limited ability as a disinfectant and are often irritating to the eye, as will be outlined below.

DETAILED DESCRIPTION OF THE INVENTION

Peracetic acid is well known as a far superior microbicide to hyrdrogen peroxide. As an anti-viral agent, 0.2% by weight peracetic acid inactivates most viruses in five minutes. Kline LB, Hull RN. "The virucidal properties of peracetic acid." *American J. Clin. Pathol* 1960; 33:30–33. $H_2O_2$ required a 15 fold higher concentration (3%) for the same effect. Sproessig M, Muecke H. "Virus disinfection by peracetic acid in the presence of alcohols." Wiss. Z. Humboldt-Univ. Berlin, Math.-Naturwiss. Reije 1969; 18 (6): 1171-3. Another study compared the bactericidal, fungicidal and sporicidal properties of hydrogen peroxide and peracetic acid. Baldry MGC. "The bactericidal, fungicidal and sporicidal properties of hydrogen peroxide and peracetic acid." *Journal of Applied Bacteriology* 1983: 54: 417–423. $H_2O_2$ was found to be a weak bactericide at the 3% concentration. It never produced a "total kill" even after four hours. Peracetic acid, however, in only a 0.01% concentration had a total kill against a wide variety of bacteria in under one minute. Against a variety of fungi, peracetic acid produced a total kill in under five minutes at a concentration of 0.1%. Sporicidal activity for peracetic acid requires only a 0.1% concentration for one hour, while $H_2O_2$ is sporicidal after three hours at a 3% concentration. As can be seen, contrary to accepted usage in the contact lens industry, $H_2O_2$ is a poor microbicide. Peracetic acid, on the other hand, is a very effective microbicide.

This invention comprises soaking the lenses in a composition containing peracetic acid, allowng enough time and concentration to effectively kill all microbes. This invention further comprises methods of decomposition by catalysts, neutraization by chemicals and/or removal by dilution(s) the peracetic acid from the contact lens and surrounding disinfecting composition.

The peracetic acid ($CH_3COOOH$) is decomposed and/or neutralized to acetic acid ($CH_3COOH$), hydrogen peroxide ($H_2O_2$) water ($H_2O$), and oxygen ($O_2$). $H_2O_2$ is further reduced to water ($H_2O$) and oxygen ($O_2$) as the following reactions show:

$$CH_3COOOH + H_2O = CH_3COOH + H_2O_2$$

$$2CH_3COOOH = 2CH_3COOH + O_2$$

$$2H_2O_2 = 2H_2O + O_2$$

The above three reactions go to the right in the presence of catalysts or neutralizing agents. The acetic acid is further neutralized to sodium acetate ($CH_3COO.Na$) using sodium carbonate ($Na_2CO_3$) or sodium bicarbonate ($NaHCO_3$), as the following reactions show:

$$Na_2CO_3 + 2CH_3COOH = 2CH_3COO.Na + CO_2 + H_2O$$

$$NaHCO_3 + CH_3COOH = CH_3COO.Na + CO_2 + H_2O$$

(Of course, other biocompatible neutralizing compounds for the acetic acid can be used instead, e.g. potassium bicarbonate.)

It is important to note that all reactions yield very safe, non-irritating, bicompatible compounds (i.e. $H_2O$, $O_2$, $CO_2$). The fourth product is sodium acetate, a substance normally found in the eye, and can be used as a tonicity agent.

One method of practicing the invention is to decompose the peracetic acid in the lens and surrounding solution by use of a peracetic acid decomposition catalyst. Metals of Periods 4, 5 and 6 of the Periodic Chart of the Elements and the Lanthanide elements (series) can be used as decomposition catalysts. Specifically the metals iron, copper, cobalt, chromium, manganese, platinum, zinc, and mercury and the element carbon are particularly effective.

A catalytic amount of one or more of the above decomposition catalysts, sufficient to remove most of the peracetic acid from the lens and surrounding solution within 8 hours (overnight), is introduced into the contact lens disinfecting system (container). The catalyst can be used in any suitable form; e.g. solid, mounted on a carrier, chemically combined with an anion etc., tablet, power, aqueous solution or plurality of particles.

In one embodiment of this method a metallic catalyst is mounted on a carrier. This "solid" catalyst, the peracetic acid composition (containing peracetic acid and optionally stabilizers. $H_2O_2$ and/or acetic acid) and the contact lenses can be introduced into the lens disinfecting system (container) at the same time (a "one step" method). Although the catalyst begins to decompose peracetic acid immediately, it usually takes up to 6 hours to complete. Thus sufficient initial concentration of peracetic acid will insure effective disinfection. The patient returns after allowing enough time for the catalytic decomposition to occur, and the lenses are ready to wear.

Alternatively, in a variation of the above embodiment, the metal catalyst (mounted or tablet, etc.) can be introduced after disinfection is completed (a "two-step" method). The original peracetic acid composition can optionally be discarded and replaced by sterile saline at the time the catalyst is introduced. The catalyst then begins to decompose the peracetic acid from the lenses and surrounding solution.

A second method of practicing the invention is to neutralize the peracetic acid in the lens and surrounding solution by use of a chemical neutralizer. Chemical neutralizers for peracetic acid include the categories of reducing agents and bases. Specifically, the chemicals sodium thiosulfate, sodium thiosulfate pentahydrate, sodium metasulfite, sodium sulfite, sodium bisulfite, phosphorous pentoxide, ascorbic acid, and isoascorbic acid are reducing agents and are particularly effective neutralizers of peracetic acid. Specifically, the chemicals sodium hydroxide, sodium carbonate and sodium bicarbonate are bases and are effective neutralizers of peracetic acid. Similar potassium compounds can also be used.

A stoichiometric amount of one or more of the above chemical neutralizers of peracetic acid is introduced into the contact lens disinfecting system. An excess can be used as insurance or to increase the speed or thoroughness of removal of peracetic acid. The chemical neutralizer can be used in any suitable form, e.g. tablet, powder, aqueous solution or plurality of particles.

The removal of peracetic acid is effective and thorough and results in residual concentrations far lower than the 100 to 400 ppm by weight disclosed in French Patent No. 2,584,503, and does so without exposing the sterilized lenses to the full range of microbes found in flowing tap water (whose suggested usage occurs in U.S. Pat. No. 4,743,447).

Disinfecting solutions of peracetic acid are often used in a concentration from 0.0001% to 10.0%. This generally comes commercially in an equal percentage concentration of acetic acid, a one sixth concentration of $H_2O_2$, and stabilizers. Typical concentrations for sterilizing contact lenses will be 0.01% to 0.1% peracetic acid, with proprotionately higher percentages of $H_2O_2$ and acetic acid to stabilize the concentration of peracetic acid. Peracetic acid may also be used in its pure form with other stabilizers employed for stability. Other chemicals, such as a nonionic surfactant as a cleaning agent, can be included in the peracetic acid disinfecting composition.

Any amount of $H_2O_2$ present in the disinfecting solution, or amounts which may form during the catalytic or chemical removal of peracetic acid, can be removed by many of the same decomposition catalysts and chemical neutralizers which are effective for peracetic acid. Catalysts and chemicals specific for removing $H_2O_2$ can also be introduced into the contact lens disinfection system (U.S. Pat. Nos. 3,912,451, 4,568,517, 4,585,488, 4,521,375, 4,473,550, 4,588,586), in addition to those intended to remove peracetic acid.

Catalysts which can decompose $H_2O_2$ include carbon, nitrogen, silica, chlorine, bromine and iodine, the metals of Periods 4, 5 and 6 of the Periodic Chart of the Elements and the Lanthanide elements including specifically copper, gold, silver, nickel, palladium, platinum, iron, osmium, manganese, molybdenum, chromium, vanadium, cobalt, magnesium, zinc, cadmium, mercury, lead, selenium and polonium, and the bio-catalysts (enzymes) catalase and peroxidase.

Chemicals which can neutralize $H_2O_2$ include sodium pyruvate, sodium thiosulfate, sodium sulfite, sodium bisulfite, sodium metasulfite, thiourea, thioglycerol, sodium formate, ascorbic acid, isoascorbic acid, oxalic acid, glyoxylic acid and tartaric acid.

Acetic acid present in the disinfecting solution (as well as acetic acid which forms during the catalytic or chemical removal of peracetic acid) can be easily neutralized by sodium carbonate or sodium bicarbonate, etc.

A third method of practicing this invention is to remove the peracetic acid from the lens and surrounding solution by removing the $H_2O_2$ and/or acetic acid (both present in the disinfecting solution and/or formed during chemical breakdown of peracetic acid) by use of the known $H_2O_2$ decomposition catalysts and/or $H_2O_2$ neutralizing compounds and/or acetic acid neutralizing compounds identified above. The removal of $H_2O_2$ and/or acetic acid from the solution moves to the right the equilibrium of the reaction of peracetic acid to $H_2O_2$ and acetic acid. This increases the spontaneous rate of decomposition of peracetic acid, thereby effectively removing the peracetic acid from the disinfecting solution.

Any combination of the above peracetic acid decomposition catalysts and chemical neutralizers, $H_2O_2$ decomposition catalysts and chemical neutralizers, and/or acetic acid neutralizers, in amounts sufficient to decompose, neutralize and/or remove the peracetic acid from the lens and surrounding solution within 8 hours, can be employed.

Many other biocompatible and desirous compounds can also be included with the catalysts and/or neutralizers to be introduced into the peracetic acid disinfecting system. Examples are a boric acid buffer system to stabilize final acidity, and importantly, tonicity agents such as NaCl to make the final solution isotonic to human tears (making unnecessary the need to rinse the sterilized lenses in isotonic saline solution prior to putting on the eye).

It is to be appreciated that following the decomposition/neutralization and/or removal of peracetic acid in the lens disinfection system, including one-step methods, the patient (especially those with sensitive eyes) may soak the contact lenses in sterile saline for ten minutes just prior to use.

We have discovered that peracetic acid decomposition catalysts containing the metal zinc (or the element zinc as in zinc chloride) are particularly advantageous. It has been shown that zinc is present in relatively high levels in ocular tissue and that it is even beneficial to the eye. Catalysts containing zinc therefore provide a dual ability: They remove the peracetic acid and then the residual zinc concentration in or on the lens provides a tonic effect for the eye. These two combined effects of the use of a zinc catalyst may even create a synergistic effect with respect to lessening the overall irritation to the eye, which is a common problem of contact lens wearers.

We have also discovered that the use of ascorbic acid as a peracetic acid chemical neutralizer is particularly advantageous. It has been shown that ascorbic acid is present in relatively high levels in ocular tissues and fluids. Ascorbic acid is commonly known as Vitamin C and is both exogenously necessary to and a constituent of all bodily tissues, as well as being totally innocuous. It even has a mild bacteriocidal and bacteriostatic effect, which is very important when dealing with the eye.

Peracetic acid neutralizing chemicals containing ascorbic acid or ascorbate compounds provide the dual ability of first removing the peracetic acid and then the residual ascorbic acid concentration in or on the lens provides a tonic effect for the eye. This may even create a synergistic effect in lessening the overall irritation to the eye.

This invention further contemplates the use of a coating to encase or encapsulate the tablet(s), granules or particles, etc. containing the peracetic acid decomposition catalyst(s) and/or chemical neutralizer(s) for peracetic acid, $H_2O_2$ and/or acetic acid and optional additional compounds employed.

The purpose of the coating is to serve as a time-delay mechanism. A sufficient length of time passes before the tablet(s), granules or particles, etc. dissolve into the solution. During this length of time the contact lenses and surrounding solution are sterilized by the peracetic acid. When the tablet has dissolved, the tablet's ingredients then decompose and/or neutralize the peracetic acid. Allowing enough time for the decomposition/neutralization process to occur (a convenient time period is anything less than 6 hours), the lenses can then be worn.

The thickness of the coating is calculated to allow a sufficient interval of time for adequate disinfection to occur before dissolving. Variations in the initial concentration of peracetic acid used will affect the thickness needed and can readily be calculated. A small excess thickness of coating can be employed to insure adequate disinfection time.

Suitable materials for this coating include organically modified cellulose, such as hydroxypropylmethyl cellulose, ethyl cellulose, cellulose acetate phthalate, and hydroxypropyl cellulose, or polyvinyl alcohol and dibutyl phthalate.

Stronger concentrations of peracetic acid can sterilize to certain degrees of efficacy in brief intervals of time (2 to 5 min). It is to be appreciated that for short time-delay intervals, those skilled in the art of manufacturing tablets etc. may be able to manufacture or compress the tablet in such a way as to effectively "time-delay" its dissolving (for that brief sterilization interval) without necessarily having to add a "coating" to the tablet.

One significant advantage of the use of a coating is that it makes unnecessary the additional step of having to open up the contact lens sterilizing system (after sterilization has occurred) and having to put in the tablets(s) at that time (a "one-step" method.)

In a preferred embodiment the coated tablet(s) containing the decomposing/neutralizing agents, the peracetic acid composition and the contact lens can be introduced into the lens disinfecting system (container) at the same time (a "one step" method). After a certain interval of time (during which disinfection and then decompositon/neutralization occur), the lenses are ready for wear (or can be stored).

It is to be appreciated that in other embodiments the peracetic acid composition can be discarded (following disinfection) and one or more aqueous dilutions made (to reduce the concentrations of peracetic acid composition) in order to enhance hypoallergenicity, before introducing the tablet(s) or coated tablet(s) containing the decomposing/neutralizing agents, or a solid metallic catalyst, etc.

Our invention contemplates another novel concept for disinfecting contact lenses with peracetic acid. Peracetic acid has the ability to be bacteriocidal or at least bacteriostatic across a wide range of concentrations. In the embodiments set forth above the original peracetic acid composition is discarded and one or more aqueous dilutions are made prior to decomposition/neutralization. It has been discovered that the residual amount of peracetic acid left in and on the lens and container walls etc. can provide a sufficient concentration of peracetic acid to again be bacteriocidal or bacteriostatic after the first dilution. This effect can hold for one or more dilutions (which are discarded), depending on the initial concentration of peracetic acid, the volume of the dilutions, and the degree of bacteriocidal/bacteriostatic capability and assuredness desired in the final dilution.

The lenses can also be stored with indefinite sterility in one of the bacteriostatic dilutions, with decomposition/neutralization done later when the lenses are desired to be worn.

The practical value of our discovery is that the dilution(s) do not have to be commercially sterilized: inexpensive distilled water or distilled water heat sterilized by the patient could be used (optionally with a salt tablet to provide tonicity, etc.). The residual peracetic acid sterilizes the next dilution volume, and the dilution lowers the concentration of all potential irritants including the peracetic acid. Less peracetic acid concentration also means less decomposing/neutralizing agent is needed (again reducing possible irritation) or less time and/or greater thoroughness for decomposition/neutralization.

It has been discovered that because of the ability of peracetic acid to disinfect across a wide range of concentration (and over one or more successive dilutions), the decomposition/neutralization step can be avoided.

If the initial concentration of peracetic acid, the number of dilutions and volume of the dilutions are calculated properly, then the final bacteriocidal/bacteriostatic dilution will have a concentration roughly in the range of 10 to 100 ppm of peracetic acid.

It has been discovered that at this point one can soak the lenses in a volume of sterile saline for roughly 10 minutes, thereby reducing the concentration to a fairly innocuous 1 to 10 ppm while still maintaining sterility. The lenses can then be worn. The advantage of this method is low expense, but the disadvantages are the number of steps required and that patients with more sensitive eyes may require the thorough decomposition/neutralization of peracetic acid disclosed above.

Other hygienic and medical articles in addition to contact lenses which can be treated by the methods disclosed above include, for example, dental prostheses or ear inserts of hearing aids.

We have also discovered a simple yet novel all purpose contact lens rising and diluting solution which is sterile, comprising ascorbic acid and water. Ascorbic acid is bateriostatic and bacteriocidal and can be used in any concentration from 1 ppm to that which is isotonic to human tears. Sodium chloride etc. can be added to adjust lower concentrations up to isotonicity, and other compounds can be added such as a boric acid buffer system to balance acidity.

An ascorbic acid sterile saline can be used as a dilution volume to lower the concentrations of any disinfecting composition, including peracetic acid, or cleaning solution, from contact lenses. It can be prepared commercially, but importantly it can be prepared inexpensively at home from distilled water, sodium chloride, etc. tablet, and ascorbic acid. To increase sterility, the distilled water and salt tablet, etc. can be heat sterilized, with the ascorbic acid added afterwards or prior to use. It is possible to heat sterilize the ascorbic acid also with the distilled water and salt, guaranteeing a high level of sterility. As noted above, ascorbic acid is necessary for human tissues (Vitamin C) and has a tonic effect on the eye.

EXAMPLE 1

An inert plastic substrate with a platinum coating was placed in a cylindrical container. 15 ml. of peracetic acid solution (0.1% peracetic acid, 0.1% acetic acid, 0.02% $H_2O_2$) was poured into the container, and a tablet composed of 99 mgs. NaCl and 24 mgs. $Na_2CO_3$ was added to the solution. The $Na_2CO_3$ was used to neutralize the acetic acid. The sodium acetate formed and the NaCl in the 15 ml. of solution formed a final solution isotonic to human tears (0.9% NaCl). This tablet needs no coating and will begin to dissolve after it is added.

Just after the tablet was added, a pair of soft contact lenses were placed into an appropriate holder, lowered into the peracetic acid solution, the container was sealed, and shaken to ensure the peracetic acid solution came in contact with the entire container. Catalytic decomposition (by the platinum disc) of the Peracetic acid and $H_2O_2$ took place during a six hour period (sufficient time to reduce the concentration of peracetic acid and $H_2O_2$ to below 50 ppm.) complete disinfection of the contact lenses only required 20 minutes (more time than the usual 10 minutes was needed since the concentration of peracetic acid was being reduced starting at time zero), so much more than enough time elapsed to enable disinfection to occur.

EXAMPLE 2

15 ml. of peracetic acid solution (0.1% peracetic acid, 0.1% acetic acid, 0.02% $H_2O_2$) was poured into an appropriate cylindrical container. A pair of contacts were placed in a holder, and lowered into the peracetic acid solution. The container was sealed, and shaken. After 10 minutes elapsed (to allow time for disinfection), the container was opened, and a tablet containing 63 mgs. sodium thiosulfate, 14 mgs. sodium carbonate, and 88 mgs. sodium chloride was placed in the peracetic acid solution. The container was resealed, and allowed to sit for another 10 minutes. After this time, the peracetic acid and $H_2O_2$ were neutralized to below 200 ppm, and the resultant solution was isotonic to tears.

In each of the two examples above, a single rinse with saline just before insertion onto the eye can be carried out for sensitive patients. This is done by pouring out the peracetic acid solution after neutralization, adding 15 ml. of sterile non-preserved saline, closing the container, and allowing it to sit for 10 minutes. This will dilute the concentration about 30 fold, and reduce the concentrations of peracetic acid and $H_2O_2$ to below 10 ppm.

EXAMPLE 3

Contact lenses were sterilized in 10 cc of a composition containing 0.1% peracetic acid solution for a period of ten minutes. The sterilizing composition was then discarded and replaced by 10 cc of distilled water (or saline) with the container being sealed, and the system shaken. The residual peracetic acid in and on the lenses and surrounding container was approximately $\frac{1}{3}$ cc in volume. A 30-fold dilution was effected with the resulting concentration of peracetic acid after the first dilution equal to 0.0033% or 33 ppm, which was sufficient to sterilize the distilled water (or saline). Lenses can remain in this sterile storage environment indefinitely.

When a patient wishes to use lenses sterilized as in Example 3, a decomposition catalyst or chemical neutralizer can be added to the system to thoroughly remove the remaining peracetic acid, $H_2O_2$ and/or acetic acid and render the lenses ready to wear.

Alternately, when the patient wishes to use the lenses, the first dilution (solution) can be discarded and replaced by 10 cc of a sterile saline solution, the container sealed and the system shaken and left to sit for 10 to 30 minutes. Another 30-fold dilution is thus effected rendering the concentration of peracetic acid to be 0.00011% or 1.1 ppm. The lenses are then ready for wear without need for decomposition/neutralization. (Individuals who do not have sensitive eyes may be able to comfortably tolerate residual peracetic acid concentrations in the 1 to 50 ppm range.)

We claim:

1. A method for disinfecting a contact lens comprising:
   contacting said lens with a sterilizing composition comprising about 0.0001% to 10.0% by weight peracetic acid for a time period sufficient to disinfect said lens; and
   antiseptically removing said peracetic acid from said lens after said disinfecting thereof, said removing comprising contacting said lens with a peracetic acid removing agent to leave said lens and the remaining composition sterile and biocompatible to the human eye and isotonic to human tears.

2. The method of claim 1 wherein said removing agent comprises at least one peracetic acid decomposition catalyst.

3. The method of claim 1 wherein said removing agent comprises at least one peracetic acid neutralizing compound.

4. The method of claim 1 wherein said removing agent comprises at least one dilution volume.

5. The method of claim 1 wherein said removing agent comprises a sterile saline solution.

* * * * *